United States Patent [19]

Lee

[11] Patent Number: 4,717,548
[45] Date of Patent: Jan. 5, 1988

[54] ANALYTICALLY CONTROLLED BLOOD PERFUSION SYSTEM

[75] Inventor: Albert K. Lee, Washington, D.C.

[73] Assignee: The United States of America as represented by the Secretary of the Department of Health and Human Services, Washington, D.C.

[21] Appl. No.: 421,344

[22] Filed: Sep. 22, 1982

Related U.S. Application Data

[63] Continuation of Ser. No. 157,380, Jun. 9, 1980, abandoned.

[51] Int. Cl.$^4$ ............... G01N 33/00; A61M 31/00
[52] U.S. Cl. ............................ 422/68; 604/66; 604/67; 128/635; 422/45; 422/46; 422/119
[58] Field of Search ............ 604/65, 66, 67, 31, 604/50; 128/635; 422/68, 45, 46, 119

[56] References Cited

U.S. PATENT DOCUMENTS

| | | | |
|---|---|---|---|
| 3,838,682 | 10/1974 | Clark et al. | 128/214 E |
| 3,890,968 | 6/1975 | Pierce et al. | 128/214 E |
| 3,890,969 | 6/1975 | Fischel | 128/214 R |
| 3,908,653 | 9/1975 | Kettering | 128/214 R |
| 3,910,256 | 10/1975 | Clark et al. | 128/214 E |
| 3,911,341 | 10/1975 | Carlson et al. | 318/341 |
| 4,014,206 | 3/1977 | Taylor | 128/214 E |
| 4,086,924 | 5/1978 | Latham | 128/214 R |
| 4,114,144 | 9/1978 | Hyman | 128/214 E |
| 4,231,354 | 11/1980 | Kurtz et al. | 128/1 D |

FOREIGN PATENT DOCUMENTS 1491622  4/1969  Fed. Rep. of Germany.

OTHER PUBLICATIONS

Kirk–Othmer, Encyclopedia of Chemical Technology, 2nd ed., vol. 9, p. 482 (1966).

Primary Examiner—Barry S. Richman
Assistant Examiner—T. J. Wallen
Attorney, Agent, or Firm—Browdy and Neimark

[57] ABSTRACT

A blood gas analyzer system for monitoring real-time blood gas conditions in a patient perfusion circuit during open-heart surgery and other extracorporeal blood flow situations. Sensing electrodes are employed in the blood flow path for sensing pH, $pCO_2$, $pO_2$ and temperature, and electrical circuitry is provided for generating and processing the sensed signal and also for computing a signal representing $HCO_3^-$; also, these signals are monitored in real time. When situations of metabolic acidosis, metabolic alkalosis, respiratory acidosis or respiratory alkalosis occur, the system activates a corresponding alarm and automatically switches into a compensation mode of effect a change in pump speed, which in turn changes the delivery rate of oxygenated blood to the patient. When the blood gas level returns to normal, the pump speed is likewise automatically returned to a normal value.

16 Claims, 8 Drawing Figures

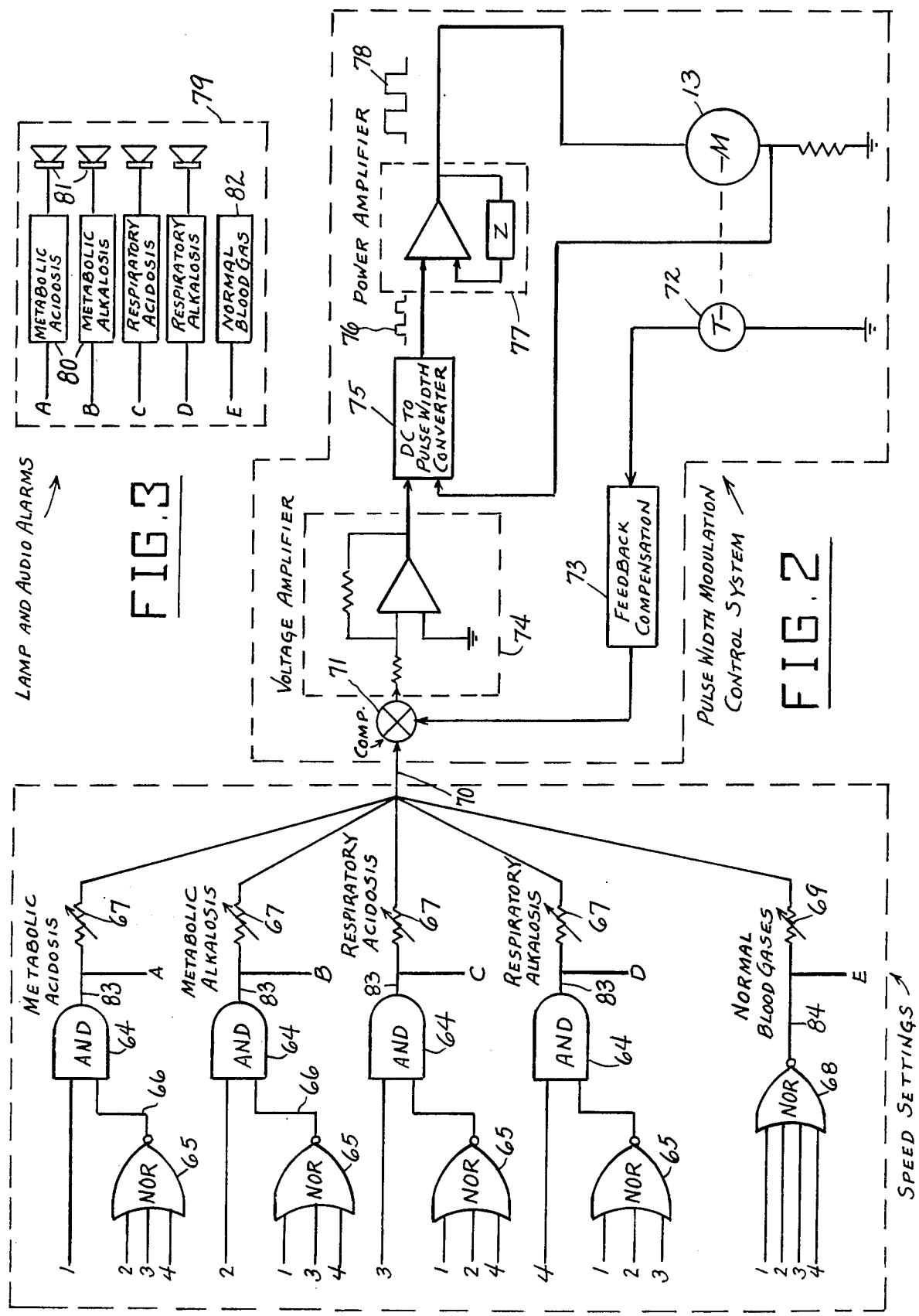

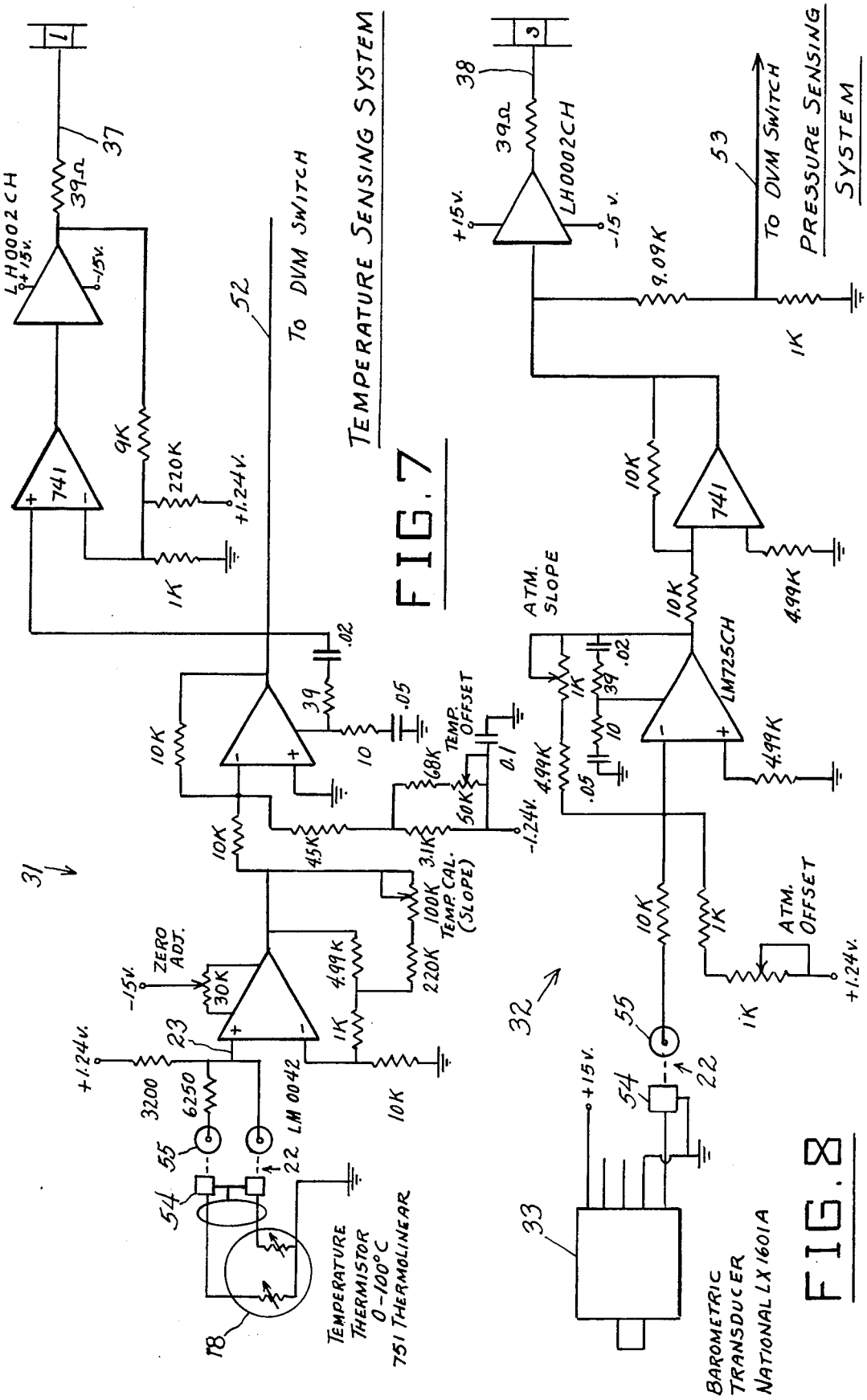

ANALYTICALLY CONTROLLED BLOOD PERFUSION SYSTEM

REFERENCE TO RELATED APPLICATION

This is a continuation of parent application Ser. No. 157,380, filed June 9, 1980, and now abandoned.

FIELD OF THE INVENTION

This invention relates to blood gas monitoring systems, and more particularly to a system for monitoring blood gases and maintaining oxygen delivery to a patient during open-heart surgery and other extracorporeal blood flow situations.

BACKGROUND OF THE INVENTION

Prior art methods of maintaining blood gas levels in extracorporeal circuits have relied on off-line determinations in a blood sample, namely, obtaining blood samples and reading out blood gas data, on a discontinuous and interrupted (periodic) basis. Thus, the determination of blood gas is made indirectly, and requires the use of a blood withdrawal apparatus, which employs very complicated and delicate electromechanical devices, subject to frequent breakdown and presenting electrical hazards. Also, the determinations frequently take a relatively long period of time, for example, from 10 to 15 minutes. From the results of the tests, the operator can initiate a change in the oxygenated blood pumping rate to compensate for conditions of metabolic acidosis, metabolic alkalosis, respiratory acidosis or respiratory alkalosis. In addition to the above drawbacks, all testing must be performed manually and sometimes requires the use of graphical or slide-rule aids. The records of blood gas data, pumping rates, and time data must be accurately maintained by the operator.

Because of the above-described disadvantages, there is a definite need for apparatus which can perform continuous real-time monitoring and recording of such important blood parameters as $pO_2$, $pCO_2$, pH, temperature, and $HCO_3^-$, and for automatically performing required corrections, such as changing oxygenated blood pumping rates, and the like, to compensate for undesired deviations of the monitored conditions, as well as for providing alarms for indicating the abnormal conditions. In particular, there is a need for apparatus providing the continuous monitoring of pH and $HCO_3^-$ for metabolic acidosis, metabolic alkalosis, respiratory acidosis, or respiratory alkalosis, and, if abnormal situations arise, activation of alarms indicating the particular metabolic or respiratory conditions and for automatically restoring the conditions to normal levels preset by the operator.

A preliminary search of the prior art revealed the following prior U.S. patents of interest:
U.S. Pat. No. 3,838,682 Clark et al.
U.S. Pat. No. 3,890,968 Pierce et al.
U.S. Pat. No. 3,890,969 Fischel,
U.S. Pat. No. 3,908,653 Kettering,
U.S. Pat. No. 3,910,256 Clark et al.
U.S. Pat. No. 4,086,924 Latham,
U.S. Pat. No. 4,014,206 Taylor,
U.S. Pat. No. 4,114,144 Hyman.

SUMMARY OF THE INVENTION

The blood gas monitoring system of the present invention overcomes the disadvantages of the previously employed systems by performing the following functions:

(1) Continuous real-time monitoring of $pO_2$, $pCO_2$, temperature, pH and $HCO_3^-$ via the Henderson-Hasselbalch equation (see Harrison, "Principles of Internal Medicine", 8th Edition, pages 376-377, McGraw-Hill, 1979.
(2) Continuous recording of the values of the above parameters.
(3) Continuous monitoring of pH and $HCO_3^-$ for metabolic acidosis, metabolic alkalosis, respiratory acidosis, or respiratory alkalosis, and, if these situations arise:
(4) Activation of alarms indicating the particular metabolic or respiratory condition detected.
(5) Automatic restoration of these parameters back to normal levels as set by the operator.

The system of the present invention is organized into the following subsystems:

(a) Blood gas electrodes and isolation circuitry.
(b) Electrometer unit, which contains the circuitry for deriving the values of $pO_2$, $pCO_2$, temperature, and pH, and the computer circuitry for determining $HCO_3^-$ from the measured pH and $pCO_2$, employing the Henderson-Hasselbalch equation.
(c) Electronic circuitry for detecting conditions of metabolic acidosis or alkalosis, respiratory acidosis or alkalosis.
(d) Alarms for indicating abnormal conditions in (b).
(e) Separate feedback control system for compensating for each abnormal condition in (b).

The function of the electrometer unit and its recorder circuitry is to continuously monitor and record, via in vivo electrodes, the real-time blood gas condition in a perfusion circuit. Separate $pO_2$ and $pCO_2$ electrodes may be employed, or a combination $pO_2$, $pCO_2$ electrode assembly may be employed, similar to that described in D. Parker et al, "Catheter-tip Electrode for Continuous Measurement of $pO_2$ and $pCO_2$", Med. & Biol. Eng. & Comput., 1978, 16, 599–600, whereas the temperature and pH sensing electrodes are available commercial items. $HCO_3^-$ can be determined from the measured pH and $pCO_2$ via the Henderson-Hasselbalch equation from the above-cited "Principles of Internal Medicine", $$pH = pK + \log \frac{HCO_3^-}{H_2CO_3} \tag{1}$$

(The pK of carbonic acid is 6.1. $H_2CO_3$ is calculated as $\alpha pCO_2$; $\alpha$, the solubility factor for carbon dioxide in body fluids is 0.031 mM/liter/mmHg of $pCO_2$. For a normal $pCO_2$ of 40, $H_2CO_3^-$ is calculated as $40 \times 0.031 = 1.2$ mM per liter).

Based on the above data, equation (1) can be rearranged as:

$$HCO_3^- = 0.031 pCO_2 \text{ antilog}(pH-6.1) \tag{2}$$

Each electrode is isolated from the signal processor via an optical isolator. The output levels of $pO_2$, $pCO_2$, pH, temperature and $H_2CO_3^-$ are displayed on panel readouts and are recorded on an event recorder, along with time. Analog level detectors are employed to test for threshold levels of pH and $HCO_3^-$ which correspond to metabolic acidosis, metabolic alkalosis, respiratory acidosis and respiratory alkalosis. The threshold levels are set by the operator. When both the pH and $HCO_3^-$ levels exceed threshold reference settings, the output of an appropriate AND gate is ON. Four different analog level detectors, each settable to a respective pair of pH and $HCO_3^-$ threshold reference levels are employed, each pair controlling a respective AND gate output. A speed control circuitry block has gating to insure that one, and only one, of the four outputs is ON at any time. If none of these are ON, a NOR gate is activated to the ON condition. Hence, in operation, five possible conditions can be detected. These states are: metabolic acidosis, metabolic alkalosis, respiratory acidosis, respiratory alkalosis, or normal blood gas.

The output voltage of the gate that is ON is adjusted by means of a variable resistor. This adjusted voltage is used to control the output speed of the pump motor by suitable means, such as by pulse width modulation. A feedback compensation signal generated by a tachometer maintains a constant adjusted output speed.

Accordingly, a main object of the invention is to provide an improved blood gas analyzing system which overcomes the deficiencies and disadvantages of previously known blood gas monitoring systems.

A further object of the invention is to provide an improved blood gas monitoring and oxygen delivering system particularly useful in extracorporeal blood circulation systems which provides real-time determinations of blood gas and which provides automatic corrections for abnormal blood gas conditions.

A still further object of the invention is to provide a novel and improved blood gas monitoring system which does not require withdrawal of blood samples for off-line determination of blood gas levels and which provides continuous monitoring of blood gas levels to enable detection of abnormal conditions such as metabolic acidosis, metabolic alkalosis, respiratory acidosis or respiratory alkalosis, which provides activation of alarms indicating abnormal states involving said conditions, and which operates automatically to restore the conditions to normal levels preset by the operators A still further object of the invention is to provide a novel and improved blood gas monitoring system which provides continuous real-time monitoring of $pO_2$, $pCO_2$, temperature, barometric pressure, pH and $HCO_3^-$ in a blood delivery circuit, which provides visual displays of and continuous recording of the values of these parameters, which detects metabolic acidosis, metabolic alkalosis, respiratory acidosis, or respiratory alkalosis, which activates alarms indicating the particular detected conditions, and which automatically restores the blood gas parameters back to normal levels as set by the operator, by suitably changing the speed of the pump motor associated with said blood delivery circuit.

DETAILED DESCRIPTION OF THE DRAWINGS

Further objects and advantages of the invention will become apparent from the following description and claims, and from the accompanying drawings, wherein:

FIG. 2 is a schematic diagram of a typical pump motor control circuit which may be employed in the monitoring system of FIG. 1.

FIG. 3 is a block diagram of the visual and audio alarm components of the system of FIG. 1.

FIG. 7 is a detailed wiring diagram of a typical temperature sensing circuit which may be employed in a blood gas monitoring system according to the present invention.

FIG. 8 is a detailed wiring diagram of a typical barometric pressure sensing circuit which may be employed in a blood gas monitoring system according to the present invention.

DESCRIPTION OF A PREFERRED EMBODIMENT

Figure 1:
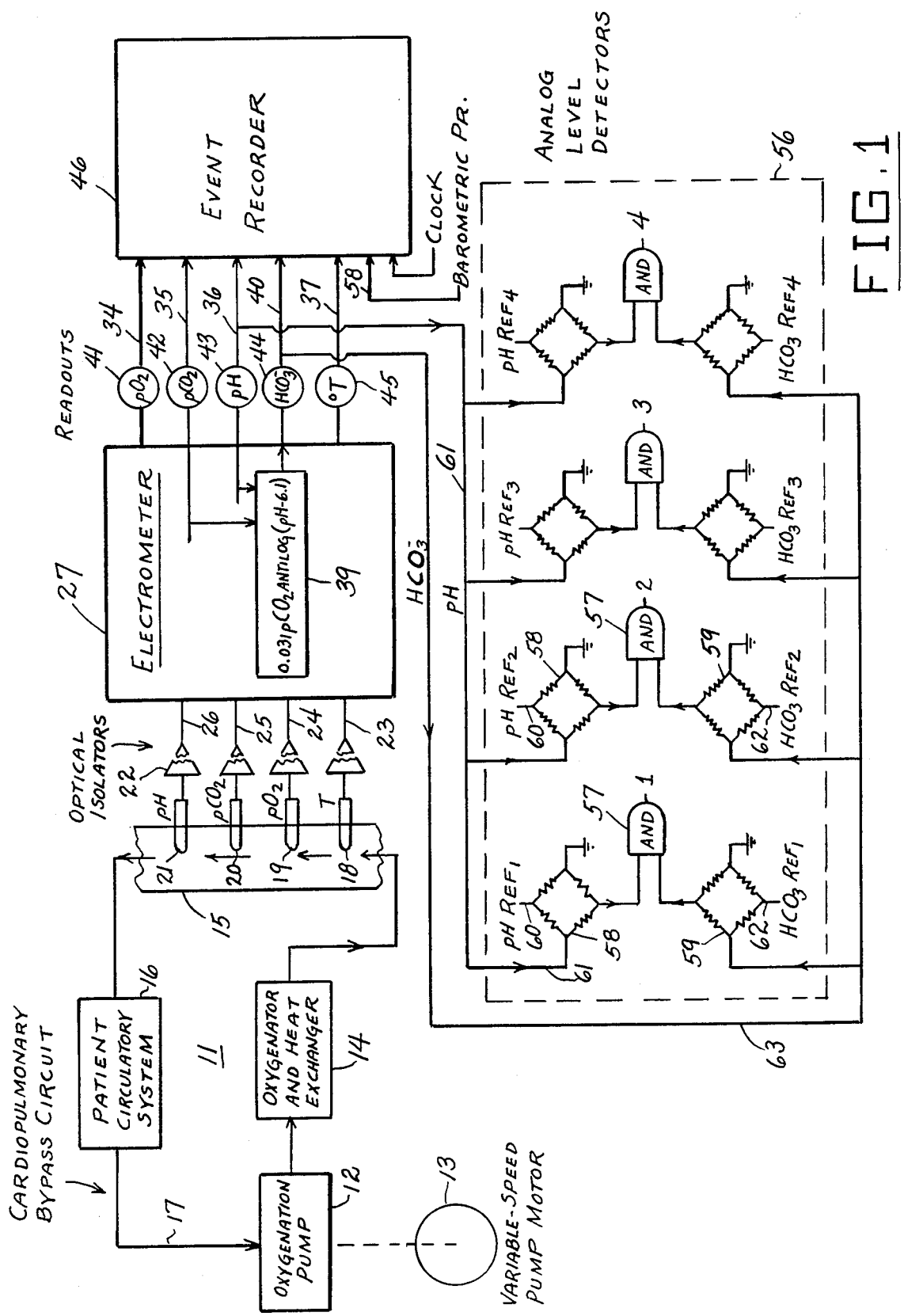
FIG. 1 is a block diagram of a blood delivery circuit provided with a blood gas monitoring system according to the present invention, schematically showing the analog level detector circuitry employed in the system, but not showing the pump motor control circuitry.
Figure 4:
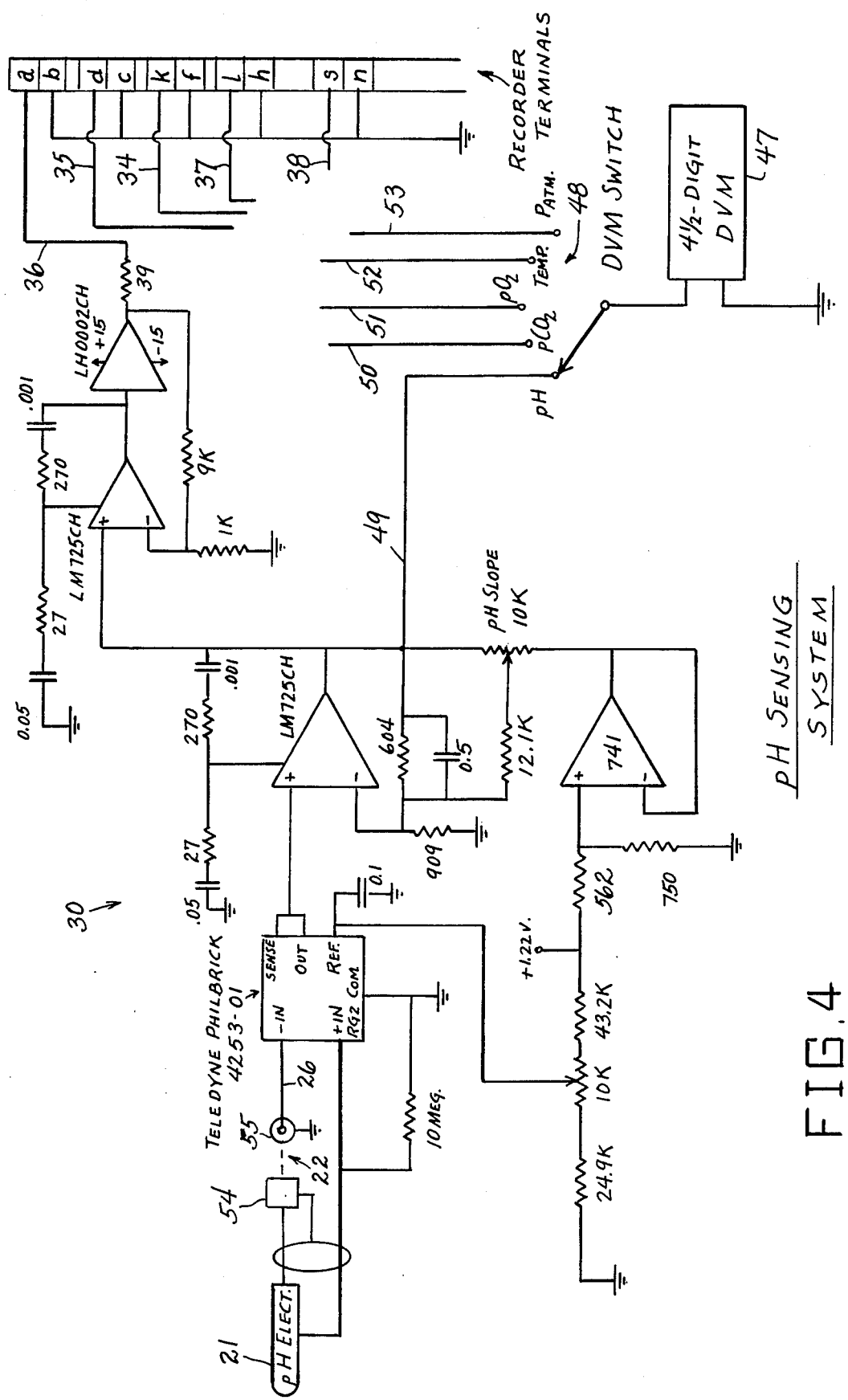
FIG. 4 is a detailed wiring diagram of a typical pH sensing circuit which may be employed in a blood gas monitoring system according to the present invention.
Figure 5:
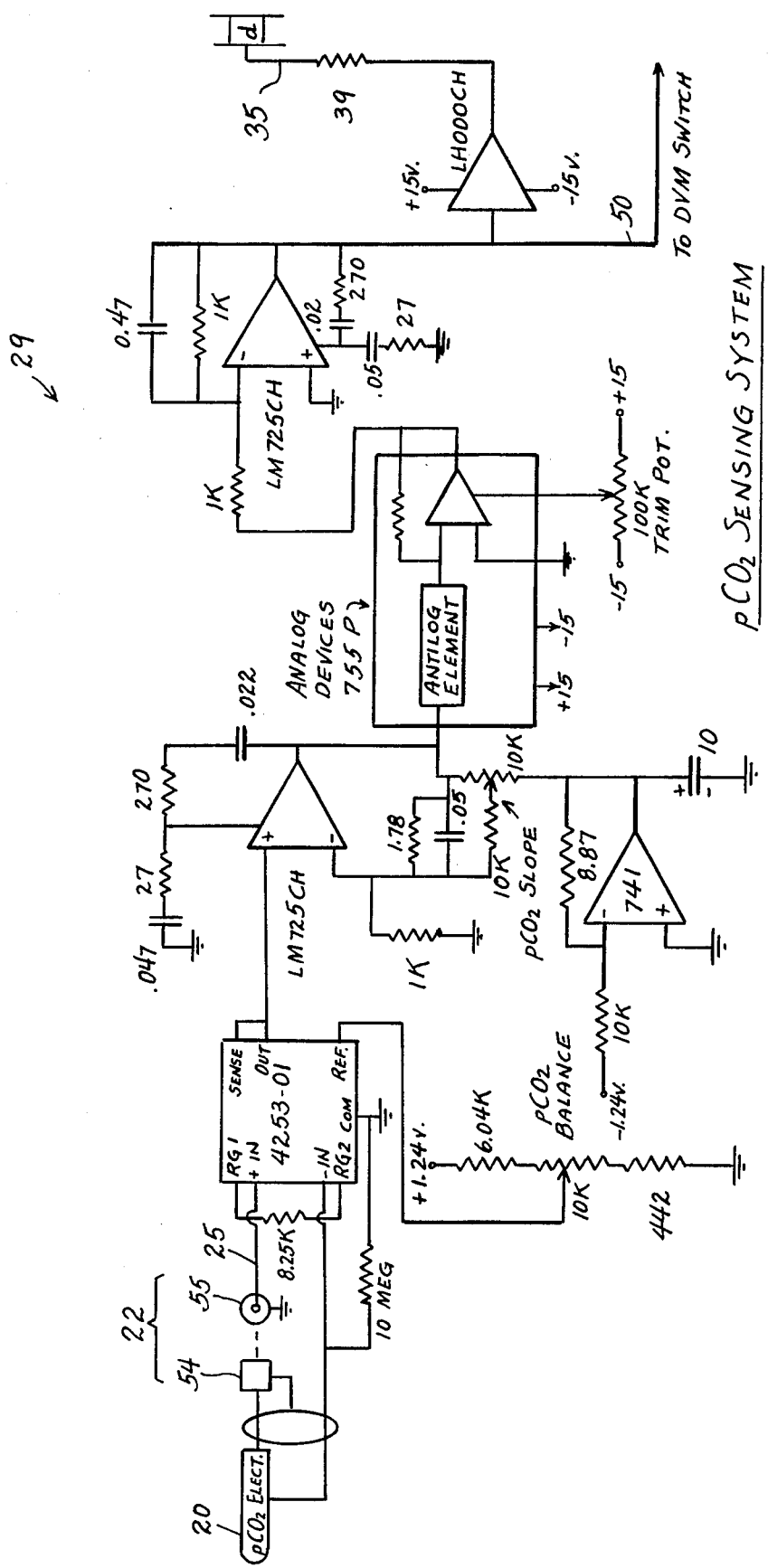
FIG. 5 is a detailed wiring diagram of a typical $pCO_2$ sensing circuit which may be employed in a blood gas monitoring system according to the present invention.
Figure 6:
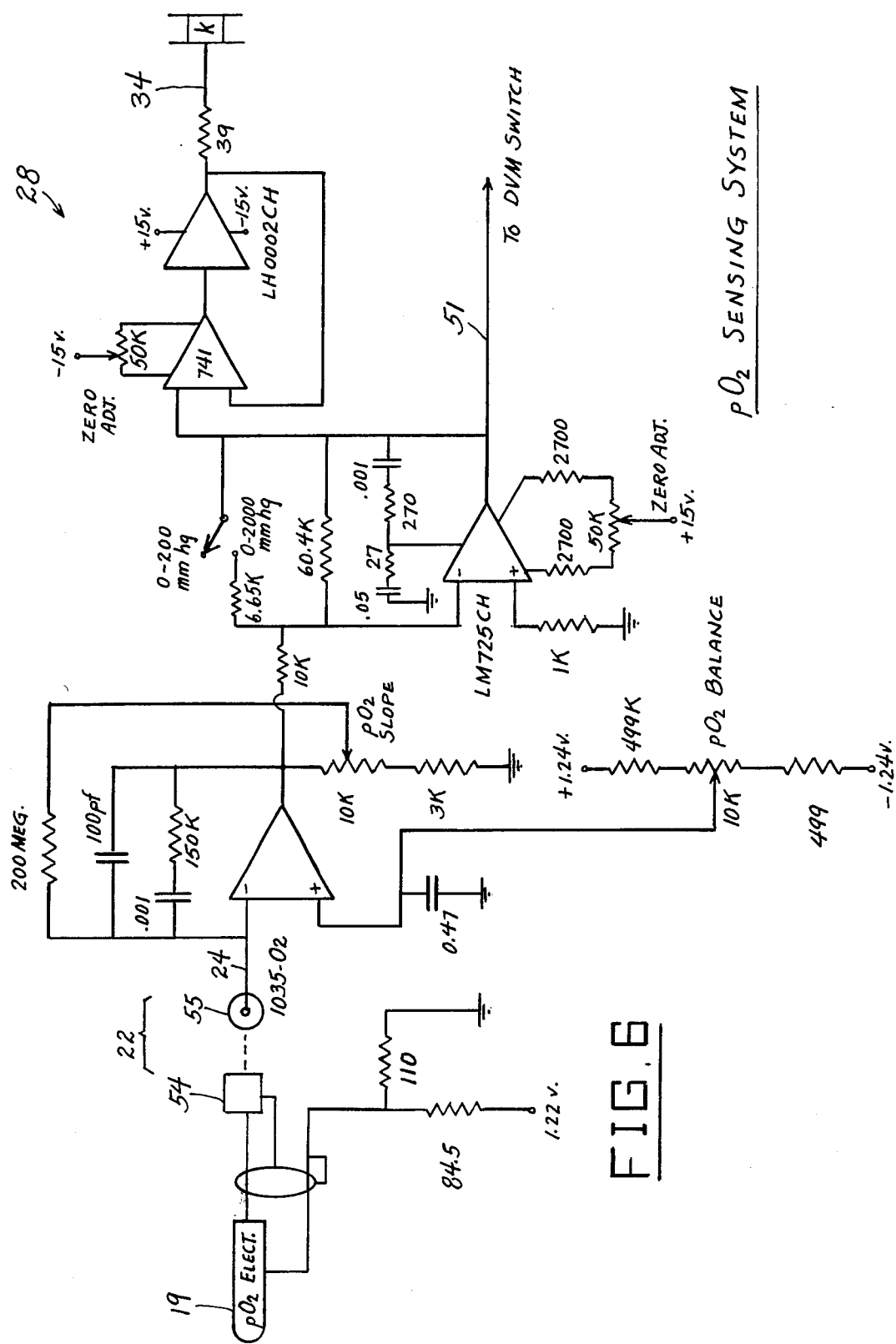
FIG. 6 is a detailed wiring diagram of a typical $pO_2$ sensing circuit which may be employed in a blood gas monitoring system according to the present invention.

Referring to the drawings, 11 generally designates a typical patient cardiopulmonary bypass circuit, generally similar to that described in U.S. Pat. No. 3,890,969 to H. Fischel. Such a bypass system is employed, for example, in cardiovascular surgery such as open-heart surgery, intensive care and surgical recovery, and is coupled to the circulatory system of the patient to revitalize and pump blood, thereby performing certain functions of the heart and lungs, and often bypassing a portion of the normal blood circulatory system. The cardiopulmonary bypass system receives venous blood feed (oxygen-deficient blood) from the patient's circulatory system, oxygenates and warms the blood, and returns the blood to the circulatory system at a flow rate corresponding to the venous drainage, thus reducing the load on the heart and lungs. In the typical bypass circuit 11 there is provided an oxygenation pump 12 driven by a variable-speed electric motor 13. The circulating blood is pumped through an oxygenator and heat exchanger 14 and a conduit 15 leading to the patient's circulatory system, designated generally at 16. The venous blood is delivered to the oxygenation pump 12 via a conduit 17.

Suitably mounted in the conduit 15 in the flow path of the oxygenated blood travelling out from the oxygenator and heat exchanger 14 are a temperature-sensing electrode 18, a $pO_2$-sensing electrode 19, a $pCO_2$-sensing electrode 20, and a pH-sensing electrode 21. These electrode devices are of conventional construction. The $pO_2$ electrode and $pCO_2$ electrode may be incorporated in a combination assembly similar to that shown in D. Parker et al, "Catheter-tip Electrode for Continuous Measurement of $pO_2$ and $pCO_2$", Medical & Biological Engineering & Computing, pages 599–600, September 1978, above cited, having respective $pO_2$ and $pCO_2$ output wires.

The electrical output signals from the sensing electrode devices are conveyed, preferably via respective optical isolators 22, to respective input lines 23 to 26 of an electrometer unit 27. The electrometer unit 27 includes respective signal processing circuits for $pO_2$, $pCO_2$, pH and temperature, illustrated respectively in detail at 28, 29, 30 and 31 in FIGS. 6, 5, 4 and 8, and also has a barometric pressure signal processing circuit 32, shown in FIG. 8, which receives output signals from a conventional barometric pressure transducer 33, shown schematically in FIG. 8, exposed to ambient barometric pressure.

The $pO_2$ signal processing circuit 28 (FIG. 6) provides a $pO_2$ output signal at its output line 34. The $pCO_2$ signal processing circuit 29 (FIG. 5) provides a $pCO_2$ output signal at its output line 35. The pH signal processing circuit 30 (FIG. 4) provides a pH output signal at its output line 36. The temperature signal processing circuit 31 (FIG. 7) provides a temperature output signal at its output line 37. The barometric pressure signal processing circuit 32 (FIG. 8) provides a barometric pressure output signal at its output line 38.

The electrometer 27 includes conventional computer circuitry 39 for computing $HCO_3^-$ from the Henderson-Hasselbalch equation, as above set forth, with respective inputs from the $pCO_2$ output signal line 35 and the pH output signal line 36, and thereby provides an $HCO_3^-$ output signal at its output line 40.

Respective visual display readout devices 41 to 45 for $pO_2$, $pCO_2$, pH, $HCO_3^-$ and temperature are provided at the respective signal output lines 34, 35, 36, 40 and 37. The output signals provided at these signal output lines are continuously recorded in a suitably clocked conventional multi-channel recorder 46, which records these analog signal outputs, along with time.

The visual display readout means for pH, $pCO_2$, $pO_2$, temperature and atmospheric pressure may include or be in the form of a digital voltmeter 47 (FIG. 4) which may be selectively connected by means of a conventional selector switch 48 to appropriately-connected signal function readout wires 49, 50, 51, 52 and 53 leading from the output portions of the respective signal processing circuits 30, 29, 28, 31 and 32.

The input circuitry of the respective signal processing circuits includes suitable electrode isolation means, such as optical links, for isolating the sensing electrodes from the remainder of the signal processing circuits. Each optical link may comprise an LED unit 54 driven by an associated sensing electrode so that the optical output varies in accordance with the magnitude of the sensed condition. Said optical output is delivered to a photosensitive transducer element 55, such as a photomultiplier tube, to convert the optical output into a corresponding electrical signal, which is thus transmitted to the input of the signal processing circuit.

The apparatus is constructed so as to detect states of metabolic acidosis and alkalosis, and respiratory acidosis and alkalosis, based upon the measured pH, $HCO_3^-$ and $pCO_2$. The apparatus can be set to provide audio and visual alerts when preset levels of pH, $pO_2$, temperature, $HCO_3^-$, metabolic acidosis and alkalosis, or respiratory acidosis and alkalosis are reached. The apparatus can, upon detection of a preset metabolic or respiratory level, switch into a correction mode whereby changes in pump speed, and, if desired, $O_2/pCO_2$ ratio may be employed to reequilibrate the patient.

Thus, as shown in FIG. 1, an analog level detector circuit 56 is provided to test for threshold levels of pH and $HCO_3^-$ which correspond to metabolic acidosis (a signal output at "1"), metabolic alkalosis (a signal output at "2"), respiratory acidosis (a signal output at "3") and respiratory alkalosis (a signal output at "4"). Analog level detector 56 comprises four threshold level detection circuits, for detection of the said condition thresholds. Each of the threshold detection circuits comprises an AND gate 57 to whose respective inputs are connected the outputs of a pH threshold sensing network 58 and an $HCO_3^-$ threshold sensing network 59. The pH network 58 is furnished at one of its inputs 60 with a pH reference voltage associated with pH threshold value for one condition, for example, metabolic acidosis. The other network input is connected by a wire 61 to pH output wire 36. The associated $HCO_3^-$ threshold sensing network 59 is furnished at one of its inputs 62 with an $HCO_3^-$ reference voltage associated with $HCO_3^-$ threshold value for said metabolic acidosis condition, and its other input is connected by a wire 63 to the $HCO_3^-$ output wire 40. When the threshold values for pH and $HCO_3^-$ are simultaneously reached or exceeded at the output wires 36 and 40, the networks 58 and 59 turn on the AND gate 57 and furnish an ON signal output at "1".

The other three threshold detection circuits of the analog level detector 56 operate in a similar manner, to detect metabolic alkalosis, respiratory acidosis and respiratory alkalosis. In each case the signal threshold levels for the signal range for each particular condition are set by the operator by providing the appropriate reference voltages at the network reference terminals 60, 62. When both the pH and $HCO_3^-$ levels (at the wires 61 and 63) reach or exceed the threshold values for the particular range, the output of the appropriate AND gate 57 is ON. The outputs of the other three AND gates 57 are necessarily OFF.

The speed control circuit for pump motor 13 is illustrated in FIG. 2. In this circuit there is gating to insure that one, and only one, of the four possible outputs of analog level detector 56 can be effectively operative at any given time to change the pump motor speed. Thus, for each of the four possible outputs ("1", "2", "3" and "4") from the analog level detector circuit 56 of FIG. 1 there is provided an AND gate 64 with which is associated a NOR gate 65. The output of each NOR gate 65 is connected via an inverter and a wire 66 to one input of the associated AND gate 64. A respective output terminal ("1", "2", "3" or "4") of the level detector circuit 56 is connected to the other input of said AND gate 64. The remaining three output terminals of the level detector circuit 56 are connected as inputs to said NOR gate 65. The four possible permutations of these connections are illustrated in FIG. 2, comprising four circuit branches, each controlled by a respective one of the four level detector outputs. Each branch includes an adjustable speed-controlling resistor 67.

The adjustable resistors 67 are set to provide pump motor speed adjustment for correcting for the four abnormal blood gas conditions, namely, metabolic acidosis, metabolic alkalosis, respiratory acidosis or respiratory alkalosis.

A fifth circuit branch, for normal blood gas conditions, comprises a NOR gate 68 and an adjustable resistor 69. The four output terminals of analog level detector 56 are connected to the input terminals of NOR gate 68. Therefore, if none of the outputs of level detector 56 is ON, the NOR gate 68 is activated to the ON condition, maintaining the pump motor at normal speed.

Hence, five possible conditions can be detected during operation, namely, metabolic acidosis, metabolic alkalosis, respiratory acidosis, respiratory alkalosis or normal blood gas.

The outputs of the respective gated branch circuits are connected via the variable resistors 67 and 69 to a common junction wire 70 leading to one input of a comparator 71. Pump motor 13 is coupled to a tachometer 72 whose output is connected to the other input of comparator 71 via a conventional feedback compensation circuit 73. The speed of motor 13 is controlled by a pulse width modulation circuit comprising a voltage amplifier 74 which is at times supplied with a correction signal from the output of comparator 71, and delivers an amplified output signal to a DC-to-pulse width converter 75, which in turn generates pulses 76 representing speed change signals. These are amplified in a power amplifier 77, forming energizing pulses 78 which are supplied to motor 13 and drive the motor at a speed in accordance with pulse width. Feedback is provided by the tachometer 72 and its compensation circuit 73 to correct the motor speed until a null output condition is reached at the comparator 71. The feedback compensation signal generated by tachometer 72 maintains a constant adjusted motor output speed for each phase of pump motor operation, in accordance with the setting of the variable resistor 67 or 69 associated with said phase.

FIG. 3 diagrammatically illustrates a visual display and audio alarm unit, designated generally at 79, which may be employed in the above-described system. The alarm unit 79 is provided with respective lamps 80 and loud speakers 81, or similar sounding devices, for the four abnormal blood gas conditions to be detected, and with a lamp 82 for indicating normal blood gas conditions. The five indicating circuits of alarm unit 79 have activating terminals A, B, C, D and E. The activating terminals A to D are respectively operatively connected to the AND gate output wires 83, and the normal blood gas lamp activating terminal E is operatively connected to the NOR gate output wire 84 of FIG. 2.

In operation, the system continuously monitors and records the real-time blood gas condition of the patient perfusion circuit, shown in FIG. 1. When situations of metabolic acidosis, metabolic alkalosis, respiratory acidosis or respiratory alkalosis occur, the system alerts the operator, for example, by means of the lamp and audio alarm assembly 79 in FIG. 3, and automatically switches into a compensation mode, employing the circuitry of FIG. 2, to effect a change in pump speed, which in turn changes the delivery rate of oxygenated blood to the patient. When the blood gas level returns to normal, the pump speed likewise automatically returns to a normal value. The above-described system can be made to operate in a patient blood bypass circuit for an extended period of time, for example, as long as 12 days, with currently available oxygenation systems, which are capable of such 12-day use.

Current standards of blood bypass systems allow for 3 hours of bypass without in-line blood gas measurement, recording, alarm or feedback compensations. Use of the system of the present invention would enable the use of much higher standards.

In the specific embodiment of the invention described above, $pCO_2$ and pH are measured and $HCO_3^-$ is calculated via analog circuitry. Alternatively, these values can be converted to digital equivalents using standard analog-to-digital conversion techniques. The derived digital data can then be used to input into appropriate digital control devices.

While a specific embodiment of an improved blood gas analyzer system has been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiment.

What is claimed is:

1. A patient blood perfusion system comprising a blood flow circuit adapted to be connected with a patient's blood circulatory system, said blood flow circuit including variable-speed pump means, blood oxygenation means and flow conduit means in circuit with said pump means and blood oxygenation means, electrode means mounted in said flow conduit means for generating electrical signals in accordance with conditions in the blood flowing in said flow conduit means, and means to vary the speed of said pump means in accordance with said electrical signals corresponding to predetermined levels of blood conditions sensed by said electrode means, and wherein said electrode means includes respective pH and $CO_2$ sensing electrodes, and said speed-varying means includes means for computing $HCO_3$.

2. The patient blood perfusion system of claim 1, and wherein said speed-varying means includes means for comparing the sensed pH level signal with a predetermined associated pH reference voltage and means for comparing the computed $HCO_3^-$ value with a predetermined $HCO_3^-$ reference voltage.

3. The patient blood perfusion system of claim 2, and wherein said speed-varying means comprises speed-changing circuit means connected to said pump means, wherein the pH reference voltage corresponds to a predetermined pH threshold value and the $HCO_3^-$ reference voltage corresponds to a predetermined $HCO_3^-$ threshold value, and means activating said speed-changing means when the sensed pH level and computed $HCO_3^-$ level simultaneously attain or exceed said pH threshold value and said $HCO_3^-$ threshold value.

4. The patient blood perfusion system of claim 3, and wherein the reference pH voltage value and the reference $HCO_3^-$ voltage value correspond to threshold values for a metabolic acidosis blood condition.

5. The patient blood perfusion system of claim 3, and wherein the reference pH voltage value and the reference $HCO_3^-$ voltage value correspond to threshold values for a metabolic alkalosis blood condition.

6. The patient blood perfusion system of claim 3, and wherein the reference pH voltage value and the reference $HCO_3^-$ voltage value correspond to threshold values for a respiratory acidosis blood condition.

7. The patient blood perfusion system of claim 3, and wherein the reference pH voltage value and the reference $HCO_3^-$ voltage value correspond to threshold values for a respiratory alkalosis blood condition.

8. The patient blood perfusion system of claim 1, wherein said speed-varying means includes means for comparing the sensed pH signal level with a predetermined fixed reference voltage corresponding to a threshold pH value and means for comparing the computed $HCO_3^-$ value with a predetermined fixed reference voltage corresponding to a threshold $HCO_3^-$ value, wherein said speed-varying means comprising speed-changing circuit means connected to said pump means, and means activating said speed-changing circuit means responsive to the simultaneous attainment of the sensed pH level to said threshold pH value and the computed $HCO_3^-$ level to said threshold $HCO_3^-$ value.

9. The patient blood perfusion system of claim 14, and wherein said speed-varying means comprises a plurality of respective pH and $HCO_3^-$ cooperating pairs of level detector circuits, each circuit pair having comparison means for comparing the sensed pH signal level with a respective threshold pH reference voltage and the computed $HCO_3^-$ level with a respective $HCO_3^-$ reference voltage, whereby to detect a corresponding plurality of different blood gas conditions, and means to selectively activate the speed-changing circuit means responsive to the simultaneous attainment of the sensed pH level to the threshold pH level and the computed $HCO_3^-$ level to the threshold $HCO_3^-$ value in any of said cooperating pairs of level detector circuits.

10. The patient blood perfusion system of claim 9, and respective alarm means associated with each of the cooperating pairs of level detector circuits, and means to selectively activate the alarm means responsive to the simultaneous attainment of the sensed pH level to the threshold pH level and the computed $HCO_3^-$ level to the threshold $HCO_3^-$ value in any of said cooperating pairs of level detector circuits.

11. The patient blood perfusion system of claim 9, and wherein the pairs of level detector circuits comprise four circuit pairs for respectively detecting blood gas conditions of metabolic acidosis, metabolic alkalosis, respiratory acidosis and respiratory alkalosis.

12. The patient blood perfusion system of claim 9, and respective indicating display means associated with each of the cooperating pairs of level detector circuits, and means to selectively activate the indicating display means responsive to the simultaneous attainment of the sensed pH level to the threshold pH level and the computed $HCO_3^-$ level to the threshold $HCO_3^-$ value in any of said cooperating pairs of level detector circuits, normal blood gas indicating display means, and means to activate said normal blood gas indicating means when none of the pairs of cooperating level detector circuits are in a concurrent threshold attainment condition.

13. The patient blood perfusion system of claim 9, and wherein the pairs of level detector circuits comprise four circuit pairs for respectively detecting blood gas conditions of metabolic acidosis, metabolic alkalosis, respiratory acidosis and respiratory alkalosis, respective alarm means associated with each of the cooperating pairs of level detector circuits, and means to selectively activate each of said alarm means responsive to the simultaneous attainment of the sensed pH level to the threshold pH value and the computed $HCO_3^-$ level to the threshold $HCO_3^-$ value in the associated pair of level detector circuits.

14. The patient blood perfusion system of claim 13, and normal blood gas indicating display means, and means to activate said normal blood gas display means when none of the pairs of cooperating level detector circuits are in a concurrent threshold attainment condition.

15. A patient blood perfusion system comprising a blood flow circuit adapted to be connected with a patient's blood circulatory system, said blood flow circuit including variable-speed pump means, blood oxygenation means and flow conduit means in circuit with said pump means and blood oxygenation means, electrode means mounted in said flow conduit means for generating electrical signals in accordance with conditions in the blood flowing in said flow conduit means, and means to vary the speed of said pump means in accordance with said electrical signals corresponding to predetermined levels of blood conditions sensed by said electrode means, wherein said variable-speed pump means comprises a pump driven by an electric motor and means to energize said motor with driving pulses of variable width, and wherein said means to vary the speed of the pump means comprises means to vary the width of said driving pulses in accordance with said predetermined sensed levels of blood conditions, wherein said electrode means includes respective pH and $pCO_2$ sensing electrodes, wherein said speed-varying means includes means for computing $HCO_3$, means for comparing the sensed pH signal level with a predetermined fixed reference voltage corresponding to a threshold pH value and means for comparing the computed $HCO_3$ value with a predetermined fixed reference voltage corresponding to a threshold $HCO_3$ value, and wherein said pump speed-varying means comprises means to change the width of said driving pulses responsive to the simultaneous attainment of the sensed pH signal level to said threshold pH value and the computed $HCO_3$ value to said threshold $HCO_3$ value.

16. A patient blood perfusion system comprising a blood flow circuit adapted to be connected with a patient's blood circulatory system, said blood flow circuit including variable-speed pump means, blood oxygenation means and flow conduit means in circuit with said pump means and blood oxygenation means, electrode means mounted in said flow conduit means for generating electrical signals in accordance with qualities of the conditions of the blood flowing in said flow conduit means, means to vary the speed of said pump means in accordance with said electrical signals corresponding to predetermined levels of said blood conditions sensed by said electrode means, said electrode means includes respective pH, $pCO_2$, $pO_2$, and temperature sensing electrodes, wherein said speed-varying means includes means for comparing the sensed pH level signal with a predetermined associated pH reference voltage and means for comparing the computed $HCO_3^-$ value with a predetermined $HCO_3^-$ reference voltage, said speed-varying means comprises speed-changing circuit means connected to said pump means, wherein the pH reference voltage corresponds to a predetermined pH threshold value and the $HCO_3^-$ reference voltage corresponds to a predetermined $HCO_3^-$ threshold value, means activating said speed-changing means when the sensed pH level and computed $HCO_3^-$ level simultaneously attain or exceed said pH threshold value and said $HCO_3^-$ threshold value, wherein said speed-varying means comprises a plurality of respective pH and $HCO_3^-$ cooperating pairs of level detector circuits, means to selectively activate the speed-changing circuit means responsive to the simultaneous attainment of the sensed pH level to the threshold pH level and the computed $HCO_3^-$ level to the threshold $HCO_3^-$ value in any of said cooperating pairs of level detector circuits, respective indicating display means associated with each of the sensing electrodes, means to selectively activate the indicating display means responsive to the simultaneous attainment of the sensed pH level to the threshold pH level and the computed $HCO_3^-$ level to the threshold $HCO_3^-$ value in any of said cooperating pairs of level detector circuits, normal blood gas indicating display means, means to activate said normal blood gas indicating means when none of the pairs of cooperating level detector circuits are in a concurrent threshold attainment condition, wherein the pairs of level detector circuits comprise four circuit pairs for respectively detecting blood gas conditions of metabolic acidosis, metabolic alkalosis, respiratory acidosis and respiratory alkalosis, respective alarm means associated with each of the cooperating pairs of level detector circuits, means to selectively activate each of said alarm means responsive to the simultaneous attainment of the sensed pH level to the threshold pH value and the computed $HCO_3^-$ level to the $HCO_3^-$ threshold value in the associated pair of level detector circuits, visual display readout means for continuous monitoring of said blood conditions, signal processing circuit means connecting said electrode means to said visual display means, wherein said variable-speed pump means comprises a pump driven by an electric motor and means to energize said motor with driving pulses of variable width, wherein said means to vary the speed of the pump means comprises means to vary the width of said driving pulses in accordance with said predetermined sensed levels of blood conditions, and wherein said pump speed-varying means comprises means to change the width of said driving pulses responsive to the simultaneous attainment of the sensed pH signal level to said threshold pH value and the computed $HCO_3^-$ value to said threshold $HCO_3^-$ value.

* * * * *